United States Patent [19]

Jess

[11] 4,013,072
[45] Mar. 22, 1977

[54] DRIP CHAMBER FOR INTRAVENOUS ADMINISTRATION

[75] Inventor: Thurman S. Jess, Mundelein, Ill.

[73] Assignee: Baxter Travenol Laboratories, Inc., Deerfield, Ill.

[22] Filed: Nov. 3, 1975

[21] Appl. No.: 628,275

[52] U.S. Cl. .................. 128/214 C; 210/DIG. 23; 210/94; 210/448; 210/436

[51] Int. Cl.² ........................................ A61M 5/16

[58] Field of Search ........ 128/214 R, 214 C, 214.2; 210/DIG. 23, 448, 446, 484, 94, 436; 55/159

[56] References Cited

UNITED STATES PATENTS

| | | | |
|---|---|---|---|
| 2,489,966 | 11/1949 | Laure et al. ............... | 128/214 R X |
| 3,631,654 | 1/1972 | Riely et al. ............... | 55/159 |
| 3,951,145 | 4/1976 | Smith ........................ | 128/214 C |
| 3,954,623 | 5/1976 | Hammer et al. ........... | 128/214 C X |

FOREIGN PATENTS OR APPLICATIONS 1,182,016  2/1970  United Kingdom ........... 128/214 C Primary Examiner—Dalton L. Truluck
Attorney, Agent, or Firm—Garrettson Ellis; Paul C. Flattery

[57] ABSTRACT

A drip chamber for use in the intravenous administration of liquids formed of a generally vertically disposed, hollow chamber provided with inlet means and outlet means, with the chamber being adapted to maintain a liquid level of the intravenous liquid to be administered, and a hydrophilic filter element disposed in the drip chamber between the inlet means and outlet means. The hydrophilic filter element is constantly wetted with the liquid in the drip chamber to permit the passage of liquid through the filter element while simultaneously blocking air. The drip chamber of this invention can also be provided with a hydrophobic filter element to facilitate the elimination of air from the drip chamber.

4 Claims, 9 Drawing Figures

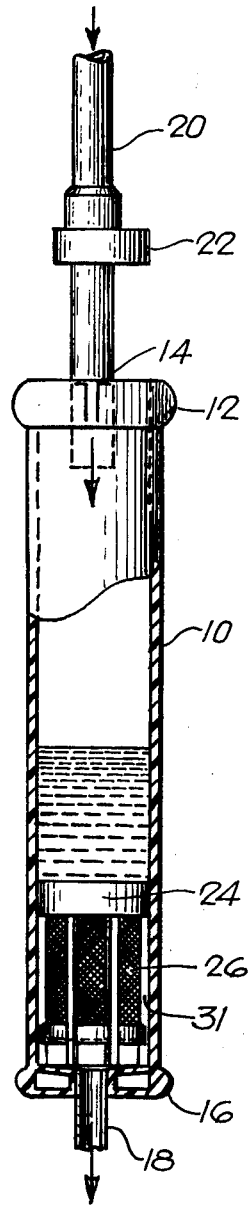
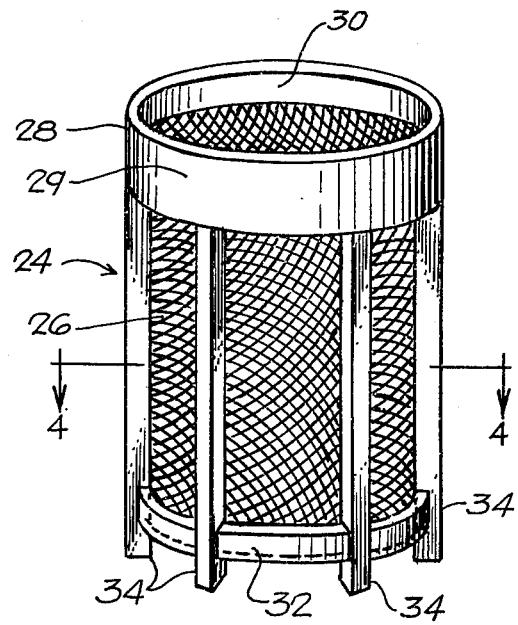
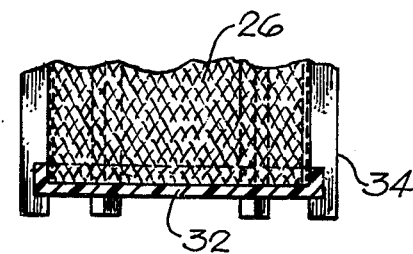
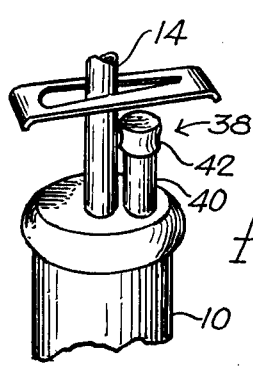
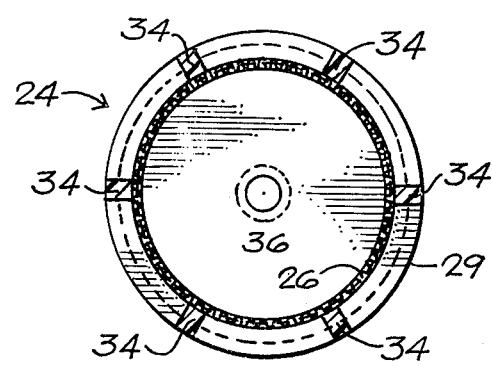

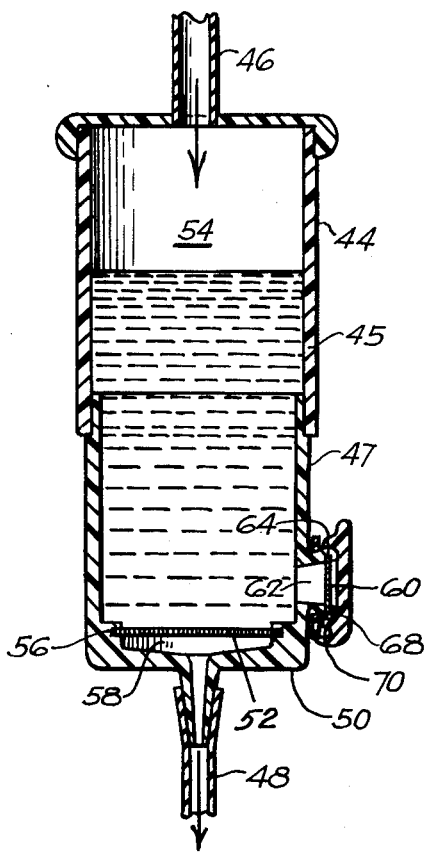
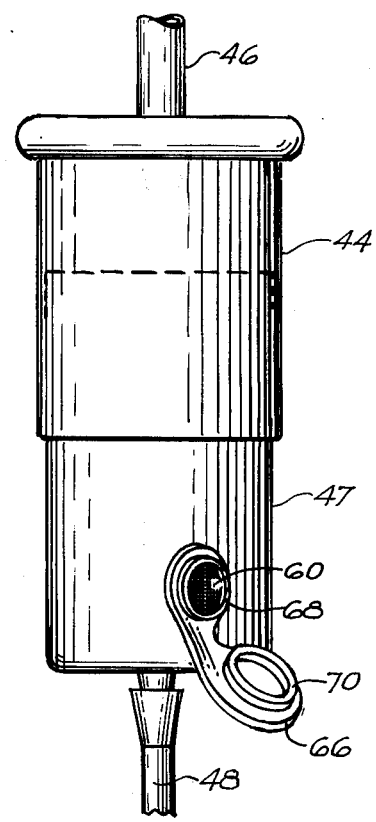
Fig. 5  Fig. 6
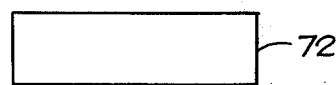
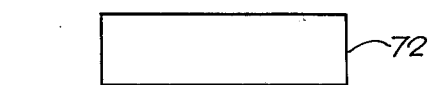
Fig. 7  Fig. 8

DRIP CHAMBER FOR INTRAVENOUS ADMINISTRATION

This invention relates to systems for administration of intravenous solutions, and more particularly, to drip chambers for use in such systems equipped with filters.

It is now common practice, in the administration of intravenous solutions, to employ what has become known in the art as a set. A container for the intravenous solution to be administered is operatively connected to a set having a drip chamber into which the liquid for administration flows. The drip chamber constitutes an important part of a set for it generally contains a drip stem (cannula) to visually determine flow rate.

The drip chamber is usually associated with a needle for insertion into the patient, the drip chamber being connected with the needle through the use of suitable tube means. With some systems, it is possible and desirable to employ mechanical pumps to maintain the desired pressure in the system. In addition, injection sites are frequently provided in the system to permit a second intravenous liquid or medication to be added to the system for administration to the patient.

It is also frequently desirable to filter solutions for intravenous administration just prior to infusion of the solution to a patient. Preferred filters are those in which the filter element has hydrophilic surface characteristics whereby the filter element, when wetted with liquid, will pass liquid therethrough but will block air. The most frequently used filter elements are filters in which the hydrophilic filter element is positioned in a separate filter from the drip chamber. One such filter of this type is described in U.S. Pat. No. 3,471,019. Filters of that type are, in use, normally attached to the patient, and thus can be rendered ineffective if the patient should change the position of the filter. For example, an air bubble present in the filter housing can spread over the surface of the hydrophilic filter element in filters of the type described in the foregoing patent, and thereby effectively cut off further fluid flow.

There is thus a need in the art for a hydrophilic filter which can be used with, or is part of, a drip chamber of an intravenous administration set, to thereby avoid any possibility that the filter can be rendered ineffective by a change in position.

It is accordingly an object of the present invention to provide a system for the administration of intravenous solutions which overcomes the foregoing disadvantages.

It is a more specific object of the invention to provide a system for the administration of intravenous solutions including a drip chamber wherein a hydrophilic filter element is included in the drip chamber whereby the hydrophilic filter element is constantly wetted with liquid to render the filter element permeable to liquids and impermeable to gases such as air.

It is yet another object of the invention to provide a drip chamber for use in the administration of intravenous liquids which is both air blocking and air eliminating whereby air contained in the drip chamber can be eliminated from the system without disassembly.

It is a further object of the invention to provide a system for the administration of intravenous solutions having a drip chamber including a hydrophilic element in which the hydrophilic filter element remains wetted after infusing the contents of a solution container, thereby blocking the passage of air (whether employing gravity flow means or mechanical pumping devices) and also permitting easy and safe restart of solution flow from another filled container without the need for repriming the system.

These and other objects and advantages of the invention will appear more fully hereinafter, and, for purposes of illustration, but not of limitation, embodiments of the invention are shown in the accompanying drawings wherein:

FIG. 1 is a partially exposed view in elevation of a drip chamber embodying the features of the present invention;

FIG. 2 is an alternative embodiment to that shown in FIG. 1 including an injection site;

FIG. 3 is a detailed view of the filter element employed in the drip chamber of FIG. 1;

FIG. 3A is a detailed view of the lower portion of the filter element illustrated in FIG. 3;

FIG. 4 is a sectional view taken along the lines 4—4 in FIG. 3;

FIG. 5 is a sectional view of an air eliminating, air blocking filter embodying the concepts of this invention;

FIG. 6 is a detailed view of the embodiment shown in FIG. 5 as to the hydrophobic filter element therein;

FIG. 7 is a schematic view of an intravenous administration set embodying the features of this invention; and FIG. 8 is an alternative intravenous administration set according to the invention.

The concepts of the present invention reside in a drip chamber for use as part of an intravenous administration set which includes an air blocking, hydrophilic filter element within the drip chamber. The drip chamber generally includes a cylindrical housing provided with inlet means at its upper portion and outlet means at its lower portion. In the practice of this invention, the drip chamber includes a hydrophilic filter element positioned within the drip chamber so as to be constantly wetted with liquid contained therein whereby the filter element is capable of passing liquid therethrough while simultaneously blocking air.

Referring now to the drawings for a detailed description of the invention, there is shown in FIG. 1 a drip chamber 10 formed of a generally cylindrical housing which is closed at its top portion 12 about an inlet tubing 14 and is closed at its bottom portion 16 about an outlet tubing 18. The tubing employed with the drip chamber of this invention is conventional and includes a hollow male connector 20 provided with a finger grip flange 22 connected to the inlet tubing 14. In this way, the male connector 20 is adapted to be connected to a source of an intravenous liquid (not illustrated in this figure).

Positioned within the drip chamber 10 is a filter 24 provided with a hydrophilic filter element 26. Such hydrophilic filter elements are, of themselves, well known to those skilled in the art. Such hydrophilic filter elements have a pore size ranging from about 0.1 $\mu$m to about 14 $\mu$m; and hydrophilic surface characteristics such that the filter element is wetted by liquid. As is well known to those skilled in the art, and is described in greater detail in the foregoing U.S. patent, such hydrophilic filter elements are capable of passing therethrough liquid while simultaneously blocking air, provided that the filter element has been wetted with liquid.

A filter element 24 is illustrated in greater detail in FIGS. 3, 3A and 4 of the drawing. A filter 24 is formed of a generally cylindrical housing 28 whose exterior dimensions correspond to the internal diameter of the drip chamber 10 whereby the filter 24 is capable of establishing a sealing relationship with the interior walls of the drip chamber 10. For example, the filter element 24 can simply be press-fitted into the drip chamber 10, or, alternatively, the filter 24 can be bonded to the drip chamber 24 to establish a sealing relationship with the drip chamber 10.

The hollow housing 28 defined by a rim portion 29 is open at its top 30 but closed by means of a bottom panel 32. Extended downwardly from the rim portion 29 are a plurality of ribs 34 which define the cylindrical walls of the housing 28. Mounted on the ribs 34 is the hydrophilic filter element 26. In the embodiment shown in FIGS. 3 and 4, the hydrophilic filter element is mounted on the interior of the housing on the ribs 34 whereby the hydrophilic filter element 26 is exposed between the ribs 34.

As is perhaps most clearly shown in FIG. 4 of the drawing, the mounting of the hydrophilic filter element 26 on the interior of the housing 28 provides an annular space between the hydrophilic filter element 26 and the interior walls of the drip chamber 10. This space, illustrated in FIG. 1 as 31, is bonded at its upper portion by the rim portion 29 in sealing engagement with the interior walls of the drip chamber 10. The space 31 defined between the hydrophilic filter element 26 and interior wall of the drip chamber 10 communicates with the discharge means 16 whereby any liquid passing through the filter element 26 enters the space 31 for discharge through the outlet means 18. In the preferred practice of the invention, as illustrated in FIGS. 3 and 3A, the ribs 34 extend below the bottom panel 32 so as to support the bottom panel 32 above the base of the drip chamber in which the filter element is mounted. In that way, liquid passing through the hydrophilic filter element 26 passes into the space 31 and flows downwardly between the ribs 34, below the bottom panel 32 into the discharge means 18.

In this way, liquid contained in the drip chamber 10 passes through the top opening 30 into the interior 36 of the filter 24 and thereby wets the hydrophilic filter element 26. Once wetted with liquid, the hydrophilic filter element 26 becomes permeable to the liquid (and impermeable to gases such as air) whereby liquid in the drip chamber 10 passes through the hydrophilic filter element 26 into the space 31 in the lower portion of the drip chamber between the ribs 34 and discharge through the downstream or exit means 16. As long as the drip chamber contains liquid to wet the hydrophilic filter element 26, that filter element will continue to pass liquid but block air from passage through the filter element.

In use, the drip chamber of this invention is connected with a suitable source of the intravenous liquid to be administered, whereby the source of liquid supplies liquid to the drip chamber 10 to establish a liquid level therein. The liquid level maintained in the drip chamber 10 serves to constantly wet the hydrophilic filter element 26 whereby the hydrophilic filter element 26 continues to pass liquid therethrough but block air. When the source of the liquid to be administered empties, the wet hydrophilic filter element prevents air from entering the outlet means so long as the hydrophilic filter element remains wet. The drip chamber can easily be reprimed by simply establishing a liquid level in the drip chamber by a fresh source of liquid, which again serves to wet the hydrophilic filter element to pass liquid and block air.

Variations in the drip chamber 10 as shown in FIG. 1 of the drawing can be made. For example, it is sometimes desirable to provide the drip chamber 10 as illustrated in FIG. 2, with an injection site generally designated as 38. This injection site includes tubing means 40 communicating with the interior of the drip chamber 10 and terminating with an elastomeric plug 42 through which a syringe may be inserted to inject a medicament into the drip chamber 10 for administration with the liquid contained therein to the patient. The injection site 38 may also be used to remove air trapped in the hollow interior of the drip chamber 10. For this purpose, a syringe can be inserted through the injection site to withdraw air from the interior of the drip chamber 10. The injection site 38 may also be used to add air to the drip chamber if it has been flooded or overfilled with solution, thereby establishing a liquid level below the drip stem (cannula) necessary for visual determination of flow rate by counting the drips falling from the drip stem.

It is sometimes desirable to provide the drip chamber with hydrophobic filter means to permit the elimination of air from the drip chamber. Hydrophobic filter elements are, of themselves, well known to those skilled in the art, and are formed of a filter element having hydrophobic surface characteristics. Such hydrophobic surface characteristics tend to cause the hydrophobic filter element to repel liquid so as to pass air therethrough. The hydrophobic filter element may likewise be employed to add air to the drip chamber for the purpose noted above.

One embodiment of a drip chamber embodying both an air blocking, hydrophilic filter element and an air eliminating, hydrophobic filter element is shown in FIG. 5 of the drawing. As is shown in this figure, the drip chamber 44 includes conventional inlet means 46 and outlet means 48 communicating with the interior of the hollow drip chamber 44. The base 50 of the drip chamber in the embodiment shown in FIG. 5 is provided with a hydrophilic filter element 52 interposed between the interior 54 of the drip chamber 44 and the outlet tubing means 48. While the precise details as to the manner in which the hydrophilic filter element is positioned at the base of the drip chamber are not critical, in the embodiment shown in FIG. 5, the drip chamber is provided with a generally circular bottom panel having an annular groove 56 into which the hydrophilic filter element 52 is secured in a sealing relationship. In this way, the liquid in the interior 54 of the drip chamber 44 is in contact with the hydrophilic filter element 52 whereby the hydrophilic filter element 52 is constantly wetted with liquid so as to be capable of passing liquid therethrough while simultaneously blocking air. The base panel 50 defines a chamber 58 on the downstream side of the hydrophilic filter element 52 into which the liquid passes through the hydrophilic filter element 52 follows for discharge through the outlet means 48.

In the embodiment shown in FIG. 5, the air eliminating capability if provided by way of a hydrophobic filter element 60 which is mounted over an opening 62 in the lower cylindrical wall of the drip chamber 44. The hydrophobic filter element can be mounted over the opening 62 in any desired manner such as by positioning it in an annular groove designated 64 as shown in FIG. 5.

In this embodiment of the invention, the hydrophobic filter element 60 is provided with a closure 66. That closure, which is adapted to engage in a sealing relationship with the nipple 68 in which the hydrophobic filter is mounted by means of an annular flange 70, serves two purposes. First, it enables the filter illustrated in FIGS. 5 and 6 to be operated in just an air blocking manner, when such operation is desired. In addition, the cap 66 can be used when the drip chamber is primed with liquid to prevent air from being drawn into the drip chamber. To commence operations with the filter of FIGS. 5 and 6 as an air blocking and air eliminating filter, the cap 66 is closed while the drip chamber is being supplied with liquid. The cap can then be opened for pressure infusion as, for example, pressure infusion by way of a mechanical pump, to eliminate air which may find its way into the system, such as when the solution container supplying the drip chamber empties and the mechanical pump begins to pump air. As long as the hydrophilic filter element is wet with liquid, it will prevent the passage of air through the tubing 48 to the patient.

In the embodiment illustrated in FIGS. 5 and 6, the drip chamber 44 is illustrated as being formed of an upper portion 45 and a lower portion 47, which are adapted to engage each other in a sealing relationship. As will be appreciated by those skilled in the art, it is also possible to manufacture the drip chamber 44 as an integral unit with the hydrophilic and hydrophobic filter elements positioned as described. In addition, it will be also understood that the hydrophobic filter can be completely eliminated from the embodiment shown in FIG. 5 and 6, and thus the drip chamber then is simply an air blocking filter.

The filters of the present invention are generally used to filter intravenous solutions, blood or other liquids prior to administration. They are generally used in combination with intravenous administration sets of the type schematically illustrated in FIGS. 7 and 8 of the drawing. As shown in those figures, the sets include a source 72 of the liquid to be administered which is connected by appropriate tubing means 74 to the drip chamber 76 embodying the features of this invention. The drip chamber 76, in turn, communicates with appropriate tubing 78 terminating in a needle 80 for administration of the liquid to a patient. It is frequently desirable that the intravenous administration set include an injection site for the purpose of facilitating the addition of medical preparations to the system, independent of the liquid supplied to the drip chamber. For this purpose, one of the tubing means 74 and 78, and preferably the latter, is provided with a Y injection site formed of a branch tubing 82 terminating in an elastomeric plug 84 through which a medical preparation can be injected by way of a hypodermic syringe.

In many instances of intravenous administration, it is desirable to provide pump means to control and/or facilitate the delivery of the intravenous liquid to the patient. In the embodiment shown in FIG. 8 of the drawing, the administration set is generally the same as that shown in FIG. 7, except that the tubing means 78 between the drip chamber 76 and the needle 80 includes pump means generally designated as 86. In the embodiment illustrated in FIG. 8, the pump means 86 is schematically shown as a syringe pump, details of which are well known to those skilled in the art. However, as is equally well known, such syringe pumps may be mechanically driven, or, alternatively, they may be replaced by any of a variety of mechanical pumps commercially available for pumping intravenous fluids.

It will be understood that various changes and modifications can be made in the details of construction, procedure and use without departing from the spirit of the invention, especially as defined in the following claims.

I claim:

1. In a drip chamber for use in intravenous administration of liquids, comprising an elongated, flexible, transparent hollow housing chamber defining an inlet at one end thereof and an outlet at the other end, said drip chamber being free of venting means, to permit pumping thereof for obtaining and maintaining a constant liquid level therein; hydrophilic filter means positioned adjacent the outlet port, said hydrophilic filter means defining a pore size sufficient to permit the passage of liquid and to prevent the passage of gas, when wetted, under normal conditions of use, said hydrophilic filter means defining a tubular filter structure positioned generally coaxially with said hollow chamber and spaced from the walls thereof, said tubular filter means defining an open end facing the inlet end of said elongated chamber and a closed end facing the outlet end of said elongated hollow chamber, and an annular sealing member adjacent said open end of the tubular filter for sealing the annular space between said tubular filter member and the chamber wall; whereby liquid passing through said tubular filter member enters into the bore thereof and passes through said tubular filter to the exterior thereof in the space between said filter and the chamber wall, and thereafter said filtered liquid passes through said outlet port.

2. The drip chamber of claim 1 in which ribs, positioned parallel to the axis of said tubular filter member and elongated chamber, are positioned between said filter and said chamber wall to support and position said tubular filter member.

3. The drip chamber of claim 2, as part of a solution administration set, defining means, in flow communication with said inlet port, for access to a source of parenteral solution, and means, in communication with said outlet port, for carrying a hypodermic needle for solution administration, the path of liquid flow through said set from the inlet port to the access means for parenteral solution source being free of air-blocking filter means.

4. In a drip chamber for use in intravenous administration of liquids, which comprises: an elongated, flexible, transparent chamber defining an inlet port at one end and an outlet port at the other end, a porous hydrophilic filter member positioned adjacent the outlet port within said chamber, said filter member being adapted to permit the passage of liquids, and to prevent the passage of gases, when wet, under normal conditions of use, said hydrophilic filter defining a tubular filter member positioned generally coaxially of said elongated chamber, said tubular filter member defining an open bore at the end facing said inlet port and sealed at its end facing said outlet port, and an annular sealing member adjacent said open end of the tubular filter for sealing the annular space between said tubular filter and the chamber wall; said tubular member being spaced from the walls of said elongated housing, whereby liquid passing from said inlet port to said outlet port enters the bore of said tubular filter, passes through said filter, and then passes between said filter and the housing wall to the outlet port; a lateral opening defined in said elongated chamber, and a hydrophobic filter element covering said lateral opening, said hydrophobic filter element being adapted to prevent the passage of liquid but to permit the passage of gas under pressures normally encountered during the conditions of use, and means for closing said lateral opening.

* * * * *